(12) United States Patent
Moscoe

(10) Patent No.: US 7,067,705 B2
(45) Date of Patent: Jun. 27, 2006

(54) PROCESS FOR THE PREPARATION OF 1,1-DICHLORO-3,3,3-TRIFLUOROPROPANE

(75) Inventor: Joseph J. Moscoe, Bemus Point, NY (US)

(73) Assignee: Honeywell International Inc., Morristown, NJ (US)

( * ) Notice: Subject to any disclaimer, the term of this patent is extended or adjusted under 35 U.S.C. 154(b) by 0 days.

(21) Appl. No.: 10/938,652

(22) Filed: Sep. 10, 2004

(65) Prior Publication Data

US 2006/0058560 A1  Mar. 16, 2006

(51) Int. Cl.
*C07C 17/00* (2006.01)
*C07C 19/00* (2006.01)
*C07C 21/00* (2006.01)
*C07C 23/00* (2006.01)
*C07C 25/00* (2006.01)

(52) U.S. Cl. .................. 570/101; 570/123; 570/161
(58) Field of Classification Search ............ 570/101, 570/123, 161
See application file for complete search history.

(56) References Cited

U.S. PATENT DOCUMENTS

| 5,710,352 A | 1/1998 | Tung ..................... 570/166 |
| 5,902,912 A | 5/1999 | Tung et al. ............. 570/164 |
| 6,023,004 A * | 2/2000 | Thenappan et al. ...... 570/188 |
| 6,362,383 B1 | 3/2002 | Wilmet et al. ........... 570/166 |

FOREIGN PATENT DOCUMENTS

EP  0 729 932 A1  9/1996

* cited by examiner

*Primary Examiner*—Johann Richter
*Assistant Examiner*—Chukwuma Nwaonicha
(74) *Attorney, Agent, or Firm*—Colleen D. Szuch

(57) ABSTRACT

A convenient and economical process for the preparation of 1,1-dichloro-3,3,3-trifluoropropane (HCFC-243) by the reaction of 1,1,1,3,3-pentachloropropane (HCC-240) with hydrogen fluoride in the presence of an activated hydrofluorination catalyst. Also, the selective fluorination of hydrochlorocarbons and/or hydrochlorofluorocarbons, or mixtures thereof is shown. A HCFC-243 reaction product yield of greater than 40% is obtained.

33 Claims, No Drawings

PROCESS FOR THE PREPARATION OF 1,1-DICHLORO-3,3,3-TRIFLUOROPROPANE

BACKGROUND OF THE INVENTION

1. Field of the Invention

The invention relates to the selective fluorination of hydrochlorocarbons and/or hydrochlorofluorocarbons, or mixtures thereof. More particularly, the invention pertains to a process for the preparation of 1,1-dichloro-3,3,3-trifluoropropane (HCFC-243) by the reaction of 1,1,1,3,3-pentachloropropane (HCC-240) with hydrogen fluoride in the presence of an activated hydrofluorination catalyst.

2. Description of the Related Art

It is known in the prior art to produce hydrofluorocarbons (HFC's) by reacting hydrogen fluoride (HF) with various hydrochlorocarbon and hydrochlorofluoro-carbon compounds. HFCs are typically prepared by fluorinating a chlorinated organic compound with a fluorination agent such as hydrogen fluoride in the presence of a fluorination catalyst. In recent years, there has been universal concern that completely halogenated chlorofluorocarbons might be detrimental to the Earth's ozone layer. Consequently, there is a worldwide effort to use fluorine-substituted hydrocarbons which contain fewer or no chlorine substituents. The desired products therefore are organic compounds similar to the organochlorine compound used in which the chlorine atoms have been partially or totally replaced with fluorine atoms. For example, it is known to produce hydrofluorocarbon HFC-245fa (1,1,1,3,3-pentafluoropropane) by the reaction of HCC-240fa (1,1,1,3,3-pentachloropropane) or HCC-1230 (1,3,3,3-tetrachloro-1-propene) with hydrogen fluoride (HF) either in the liquid or vapor phase. See, for example, U.S. Pat. No. 5,710,352 which teaches a method for the preparation of 1,1,1,3,3-pentafluoropropane (HFC-245fa) and 1-chloro-3,3,3-trifluoropropene (HCFC-1233) whereby 1,1,1,3,3-pentachloropropane (HCC-240fa) is fluorinated with HF in a vapor phase in the presence of a vapor phase catalyst.

Such reactions may be conducted in either the liquid or vapor phase. Generally, the liquid phase fluorination is preferred because the reaction is controlled at relatively lower temperatures which results in less by-product formation due to decomposition. Liquid phase fluorination, however, uses and generates corrosive compounds, such as, for example, hydrogen fluoride, hydrogen chloride, and catalysts such as $SbCl_5$ or $SbF_3Cl_2$, which form superacids. These superacids tend to corrode the reactor in which the reaction is conducted, even reactors comprised of corrosion-resistant materials such as Inconel 600, NAR25-50MII, Hastelloy C, Hastelloy G-30, duplex stainless steel and Hastelloy C-22. This is primarily due to the concentrations, temperatures and pressures involved and the need for oxidants such as chlorine that are used to maintain catalyst activity. Corrosion of the reactor compromises the structural integrity of the reactor and reduces its useful life. As a result of such extreme corrosive activity of the reaction system on metals, fluoropolymer lined reactors must be used. See, for example, U.S. Pat. No. 5,902,912, which teaches a process for producing hydrofluorocarbons in a fluoropolymer-lined reactor whereby a chlorinated organic compound in liquid phase and a fluorination agent are charged into the reactor and reacted to produce the hydrofluorocarbon. However, these lined reactors suffer from poor heat transfer and HF permeation of the liner, and the use of chlorine as an oxidant results in yield loss due to the chlorination of various materials, intermediates, and reactants.

It has been determined that these known processes are not economical relative to their product yield. It is consequently advantageous to have available an efficient hydrofluorination process allowing chlorine atoms to be replaced with fluorine atoms more easily and with high selectivity. The present invention provides an improved process for the preparation of hydrofluorocarbons with a high yield. The processes of the invention involve the reaction of a hydrocarbon with hydrogen fluoride in the presence of an activated fluorination catalyst. Particularly effective fluorination catalysts for obtaining a high yield include chlorides of metals from groups IV, V, XIV, and XV of the Periodic Table of the Elements that have been first activated by their reaction with hydrogen fluoride. More particularly, the invention provides a process for the preparation of 1,1-dichloro-3,3,3-trifluoropropane (HCFC-243) from 1,1,1,3,3-pentachloropropane (HCC-240) with a very high yield. HCFC-243 is an important precursor to the agricultural intermediate HCFC-233, i.e. trichlorotrifluoropropane.

SUMMARY OF THE INVENTION

The invention provides a process for the fluorination of 1,1,1,3,3-pentachloropropane to 1,1-dichloro-3,3,3-trifluoropropane comprising the steps of:
(a) contacting a fluorination catalyst with hydrogen fluoride under conditions sufficient to produce an activated fluorination catalyst; and
(b) reacting 1,1,1,3,3-pentachloropropane with hydrogen fluoride in the presence of said activated catalyst under conditions sufficient to produce a reaction product which comprises 1,1-dichloro-3,3,3-trifluoropropane.

The invention also provides a process for the preparation of 1,1-dichloro-3,3,3-trifluoropropane comprising:
a) introducing a fluorination catalyst into a vessel;
b) introducing hydrogen fluoride into the vessel under conditions sufficient to produce an activated fluorination catalyst;
c) adding 1,1,1,3,3-pentachloropropane and hydrogen fluoride to said vessel under conditions sufficient for the 1,1,1,3,3-pentachloropropane and hydrogen fluoride to react in the presence of said activated fluorination catalyst, thereby forming a reaction product which comprises 1,1-dichloro-3,3,3-trifluoropropane.

The invention still further provides a process for the preparation of hydrofluorocarbons comprising:
(a) contacting a fluorination catalyst selected from the group consisting of chlorides of metals from Groups IV, V, XIV, and XV of the Periodic Table of the Elements with hydrogen fluoride under conditions sufficient to produce an activated fluorination catalyst; and
(b) reacting a hydrocarbon with hydrogen fluoride in the presence of said activated fluorination catalyst under conditions sufficient to produce a reaction product which comprises a fluorinated hydrocarbon.

DETAILED DESCRIPTION OF THE INVENTION

The present invention provides a convenient route to produce hydrofluorocarbons, and particularly $CF_3-CH_2-CHCl_2$ (HCFC-243), in good selectivity from a hydrocarbon, such as $CCl_3-CH_2-CHCl_2$ (HCC-240), using an activated catalyst which is a chloride of a metal from one of group III, IV, V, XIII, XIV, and XV of the periodic table of elements.

For the purposes of this invention, the phrase "activated catalyst" is intended to describe a catalyst that has been "activated" or prepared by reacting it with hydrogen fluoride prior to using it to catalyze another reaction. In the process of the invention, the catalyst is activated by reacting it with hydrogen fluoride under conditions sufficient to produce an activated fluorination catalyst. Preferred catalysts among the group III, IV, V, XIII, XIV and XV metal chlorides include $CCl_4$, $SiCl_4$, $GeCl_4$, $SnCl_2$, $SnCl_4$, $PbCl_2$, $PbCl_4$, $NCl_3$, $PCl_3$, $PCl_5$, $AsCl_3$, $SbCl_3$, $SbCl_5$, $BiCl_3$, titanium chloride, tantalum chloride, tin chloride, antimony chloride, niobium chloride, boron trichloride and molybdenum chloride. In the preferred embodiment, the catalyst comprises titanium (IV) chloride ($TiCl_4$) or tantalum (V) chloride ($TaCl_5$). The reaction is preferably conducted with a preferred catalyst to hydrogen fluoride weight ratio of from about 0.001:1 to about 0.7:1, more preferably from about 0.03:1 to about 0.25:1 and most preferably from about 0.05:1 to about 0.15:1. In the preferred embodiment of the invention, the fluorination catalyst activation reaction is conduced under controlled conditions in an autoclave or other suitable vessel. Particularly, the reaction is preferably conducted at a reaction temperature of from about 50° C. to about 100° C., more preferably from about 60° C. to about 80° C., most preferably from about 65° C. to about 70° C. The reaction is also preferably conducted at a reaction pressure of from about 250 psi (pounds per square inch) to about 400 psi, more preferably from about 275 psi to about 350 psi, and most preferably from about 300 psi to about 325 psi. The reaction may also be conduced in a streaming reaction process wherein reactant streams are not necessarily contained in a pressure controlled vessel. During the reaction, hydrogen chloride (HCl) may be formed as a by-product and is preferably vented off or otherwise removed so that it does not interfere with the reaction process.

It has been found that particularly desirable results were obtained using a titanium catalyst that is activated under sufficient conditions such that $TiCl_4 + HF \rightarrow TiCl_xF_y$, wherein x+y=4. Similarly desirable results are obtained using a tantalum catalyst that is activated under sufficient conditions such that $TaCl_5 + HF \rightarrow TaCl_xF_y$, wherein x+y=5. Accordingly, the most preferred activated catalysts for use herein comprise $TiCl_2F_2$, $TiCl_3F$, $TiClF_3$, $TaClF_4$, $TaCl_2F_3$, $TaCl_3F_2$ and $TaCl_4F$ which in turn react with hydrogen fluoride to fluorinate $CCl_3$—$CH_2$—$CHCl_2$ (HCC-240). Each of the other useful catalyst described herein undergo similar activation reactions (e.g. $SnCl_4 + HF \rightarrow SnCl_xF_y$, wherein x+y=4; $SbCl_5 + HF \rightarrow SnCl_xF_y$, wherein x+y=5). The activated fluorination catalyst is then used to catalyze the fluorination reaction of a hydrocarbon, e.g. a hydrochlorocarbon, with hydrogen fluoride, resulting in a reaction product that comprises at least one hydrofluorocarbon (HFC) or hydrofluorochlorocarbon (HCFC).

The process of the invention is suited for the fluorination of one or more hydrocarbon reactants. The hydrocarbon reactant or reactants are preferably propanes, propenes, halogenated propanes or halogenated propenes. Preferred are three-carbon hydrocarbons and three-carbon hydrochlorocarbons. Examples of reactants include, but is not limited to, 1,1,1,3,3,3-hexachloropropane (HCC-230fa), 1,1,1,3,3-pentachloropropane (HCC-240fa) and 1,1,1,3-tetrachloropropane (HCC-250fb). The process of the invention is particularly suited for the fluorination reaction of HCC-240 ($CCl_3CH_2CHCl_2$) with hydrogen fluoride as catalyzed by the activated fluorination catalyst of the invention. The preferred reaction process proceeds as follows:

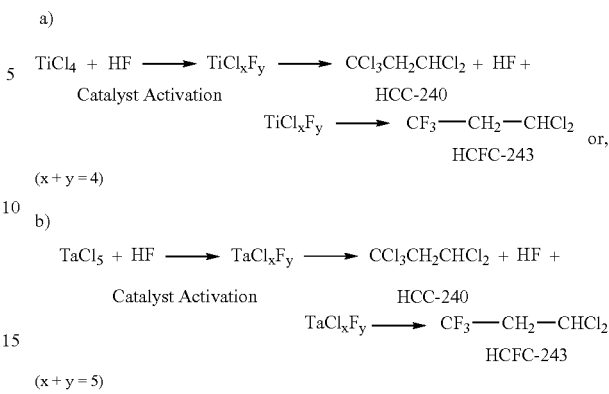

This particular reaction process is preferably conducted in an enclosed vessel, e.g. and autoclave, under similar reaction conditions as the catalyst activation reaction. Most preferably, the fluorination reaction is conducted in the liquid phase and under a vacuum in a vessel. However, it may also be suitably conduced in the vapor phase and in a batchwise or streaming manner. In the preferred embodiment of the invention, the fluorination of HCC-240 is conducted at a hydrogen fluoride to 1,1,1,3,3-pentachloropropane weight ratio of from about 5:1 to about 100:1, rmore preferably at a ratio of from about 10:1 to about 50:1 and most preferably at a ratio of from about 15:1 to about 25:1. Further, the reaction is preferably conducted at an activated fluorination catalyst to 1,1,1,3,3-pentachloropropane weight ratio of from about 0.001:1 to about 100:1, more preferably at a ratio of from about 0.025:1 to about 10:1, and most preferably at a ratio of from about 0.5:1 to about 5:1.

The reaction results in the formation of a reaction product mixture having a primary reaction product which comprises 1,1-dichloro-3,3,3-trifluoropropane (HCFC-243), and which mixture may also include unreacted starting materials and by-products that may include HCl and one or more hydrocarbons such as, for example, $CCl_3$—$CH_2$—$CHCl_2$, $CFCl_2$—$CH_2$—$CHCl_2$, $CF_3$—$CHCl$—$CHCl_2$, $CF_3$—$CH_2$—$CHClF$ and $CF_3$—$CCl$=$CCl_2$. Pure HCFC-243 may be recovered from the reaction product mixture by any means known in the art, such as by extraction or distillation. For example, the distillation may be preferably conducted in a standard distillation column at a pressure which is less than about 300 psig, preferably less than about 150 psig and most preferably less than 100 psig. The pressure of the distillation column inherently determines the distillation operating temperature. Single or multiple distillation columns may be used. Any HCl present may be recovered by operating the distillation column at from about −40° C. to about 25° C., preferably from about −40° C. to about −20° C. The aforedescribed process results in the formation of HCFC-243 with a yield of at least about 40% and greater than 70% under the most preferred conditions.

It should be understood that while the reaction process of the invention has heretofore been described in a particular sequence of steps, it is fully within the scope of the invention that the sequence of steps may vary so long as the reaction proceeds such at the reaction between hydrogen fluoride and at least one hydrocarbon, e.g. HCC-240, is catalyzed by an activated fluorination catalyst that has been separately activated by the reaction with hydrogen fluoride. Such includes the option of simultaneously contacting HF, HCC-240 (or other hydrocarbon, hydrochlorocarbon, hydrofluorocarbon, hydrochlorofluorocarbon) and activated fluorination catalyst either in a vessel or batchwise, streaming manner. Such also includes the options of first charging a vessel with HF and HCC-240 then with the activated catalyst, and also first activating the catalyst and subsequently charging the same vessel with HF and HCC-240 reactants in no particular order. The invention described herein covers all possible combinations. However, it has been found that the failure to first activate the fluorination catalyst, by separately reacting it with hydrogen fluoride, will only produce HCFC-243 in relatively low and uneconomical yields of below 40%, more particularly below 30%. Thus, the catalyst must be activated prior to reaction with a hydrocarbon reactant.

The following non-limiting examples serve to illustrate the invention:

EXAMPLE 1

An active catalyst is prepared by heating HF and Ti(IV)$Cl_4$ in the ratio 7.89:1 (to afford $TiCl_xF_y$ in which x+y=4). Subsequently, a mixture of HCC-240 $CCl_3CH_2CHCl_2$ (1,1,1,3,3-pentachloropropane), HF and the activated catalyst is heated at elevated temperature (60–100° C.). The molar ratio of HCC-240 ($CCl_3CH_2CHCl_2$ (1,1,1,3,3-pentachloropropane)) to HF is about 3:1. The ratio of reactants may be adjusted to get better selectivity of the desired product HCFC-243 ($CF_3CH_2CHCl_2$). The reaction temperature is about 50–100° C. The catalyst used is either $TiCl_4$ or TaCl5. The amount of catalyst employed is about 0.1 mol % to 25% with respect to the starting material $CCl_3CH_2CHCl_2$. Pressure is about 250–400 psi.

After the reaction, the by-product formed (mainly HCl) is removed by passing through a base solution of aqueous KOH. The reaction mixture is then quenched with water, the organic layer is separated and treated with a drying agent ($MgSO_4$), filtered and fractionally distilled to afford the desired product at ~70° C. The yield of the HCFC-243 product is from about 40% to about 70%.

EXAMPLE 2

A 450 mL autoclave equipped with a mechanical stirrer was placed under a vacuum and charged with 10.8 g (0.057 mol) of $TiCl_4$. The autoclave was then put into a dry ice container and cooled to −40° C. The cooled autoclave was then charged with 9 g (0.45 mol) HF, taken out of the dry ice container, put into a heater and heated to 75° C. to activate the catalyst, Ti(IV)Cl+HF→$TiCl_xF_y$, where x+y=4. This caused the generation of HCl and caused the pressure inside the autoclave to increase. After the pressure stopped increasing, the autoclave was taken out of the heater and cooled down to room temperature. The generated HCl was vented through a scrubber, and the autoclave was then put back into a dry ice container. Next, 30.7 g (1.53 mol) of HF was added to the autoclave, and the autoclave was then put into heater and heated to 30° C. Next, 20 g (0.092 mol) of 1,1,1,3,3-pentachloropropane (HCC-240) was added and the autoclave heated to 65–70° C. until there was no more pressure increase. The mole ratio of HF to HCC-240 was 16.6:1. The mole ratio of activated catalyst to HCC-240 was 0.61:1. Once there was no more pressure increase, the autoclave was cooled down to 25° C. and generated HCl was removed by passing through a KOH scrubber. The reaction was then quenched with 110 mL de-ionized water, the organic material was separated and dried with $MgSO_4$. Gas chromatography analysis indicated a reaction product of 72.4% $CF_3$—$CH_2$—$CHCl_2$, 7.3% $CF_3$—$CH_2$—CHClF, 7.4% $CF_3$—CHCl—$CHCl_2$, 1.1% $CFCl_2$—$CH_2$—$CHCl_2$ and <1% $CCl_3$—$CH_2$—$CHCl_2$. Pure product was obtained by fractional distillation of the crude material. $CF_3CH_2CHCl_2$ was collected at 70–71° C. at atmospheric pressure.

EXAMPLE 3

A reaction was conducted as described in Example 1 except a $TaCl_5$ (20.4 g, 0.057 mol) catalyst (Ta(V)Cl+HF→$TaClxFy$, where x+y=5) was used instead of $TiCl_4$. After the reaction, gas chromatography analysis indicated a reaction product of 0.9% $CCl_3$—$CH_2$—$CHCl_2$, 62.3% $CF_3$—$CH_2$—$CHCl_2$, 0.6% $CFCl_2$—$CH_2$—$CHCl_2$, 20.2% $CF_3$—CHCl—$CHCl_2$, and 3.3% $CF_3$—CCl—$CCl_2$.

COMPARATIVE EXAMPLE

Non-Activated Catalyst 1 mol of HCC-240, 2.935 mol of HF and 0.0712 mol of a non-activated $SbCl_5$ fluorination catalyst were reacted in a 450 mL autoclave equipped with a mechanical stirrer under similar temperatures and pressures as in Example 2. HCl generated by the reaction was vented through a scrubber. The reaction was then quenched with 110 mL de-ionized water and phase separated. Subsequent gas chromatography analysis indicated a reaction product of 40.6% HCFC-1233zd, 2.875% HCFC-123, 1.55% HCFC-244fa, <1% HCFC-243fa, 1.91% HCFC-243db, <1% HCFC-1223xd, 17.66 HCFC-242 isomer and 13.3% $C_6Cl_4F_6$ Isomer.

While the present invention has been particularly shown and described with reference to preferred embodiments, it will be readily appreciated by those of ordinary skill in the art that various changes and modifications may be made without departing from the spirit and scope of the invention. It is intended that the claims be interpreted to cover the disclosed embodiment, those alternatives which have been discussed above and all equivalents thereto.

What is claimed is:

1. A process for the fluorination of 1,1,1,3,3-pentachloropropane to 1,1-dichloro-3,3,3-trifluoropropane comprising the steps of:
   (a) contacting a fluorination catalyst with hydrogen fluoride under conditions sufficient to produce an activated fluorination catalyst; and
   (b) reacting 1,1,1,3-pentachloropropane with hydrogen fluoride in the presence of said activated catalyst under conditions sufficient to produce a reaction product which comprises 1,1-dichloro-3,3,3-trifluoropropane; and then
   c) recovering a composition consisting essentially of 1,1-dichloro-3,3,3-trifluoropropane from the reaction product.

2. The process of claim 1 wherein said fluorination catalyst comprises a material selected from the group consisting of chlorides of metals from Groups III, IV, V, XIII, XIV and XV of the Periodic Table of the Elements.

3. The process of claim 1 wherein said fluorination catalyst comprises a material selected from the group consisting of titanium chloride, tantalum chloride, tin chloride, niobium chloride, antimony chloride, boron trichloride, molybdenum chloride and combinations thereof.

4. The process of claim 1 wherein said fluorination catalyst comprises $TiCl_4$.

5. The process of claim 4 wherein said activated fluorination catalyst comprises $TiCl_xF_y$ wherein x+y=4.

6. The process of claim 1 wherein said fluorination catalyst comprises TaCl$_5$.

7. The process of claim 6 wherein said activated fluorination catalyst comprises TaCl$_x$F$_y$, wherein x+y=5.

8. The process of claim 1 wherein step (a) is conducted at a fluorinated catalyst to hydrogen fluoride weight ratio of from about 0.001:1 to about 0.7:1.

9. The process of claim 1 wherein step (a) is conducted at a fluorinated catalyst to hydrogen fluoride weight ratio of from about 0.03:1 to about 0.25:1.

10. The process of claim 1 wherein step (a) is conducted at a fluorinated catalyst to hydrogen fluoride weight ratio of from about 0.05:1 to about 0.15:1.

11. The process of claim 1 wherein the reaction of step (b) is conducted at an activated fluorination catalyst to 1,1,1,3,3-pentachloropropane weight ratio of from about 0.001:1 to about 100:1.

12. The process of claim 1 wherein the reaction of step (b) is conducted at an activated fluorination catalyst to 1,1,1,3,3-pentachloropropane weight ratio of from about 0.33:1 to about 10:1.

13. The process of claim 1 wherein the reaction of step (b) is conducted at an activated fluorination catalyst to 1,1,1,3,3-pentachloropropane weight ratio of from about 0.6:1 to about 5:1.

14. The process of claim 1 wherein the reaction of step (b) is conducted at a hydrogen fluoride to 1,1,1,3,3-pentachloropropane weight ratio of from about 5:1 to about 100:1.

15. The process of claim 1 wherein the reaction of step (b) is conducted at a hydrogen fluoride to 1,1,1,3,3-pentachloropropane weight ratio of from about 10:1 to about 50:1.

16. The process of claim 1 wherein the reaction of step (b) is conducted at a hydrogen fluoride to 1,1,1,3,3-pentachloropropane weight ratio of from about 15:1 to about 25:1.

17. The process of claim 1 wherein each of steps (a) and (b) are conducted at a temperature of from about 50° C. to about 100° C.

18. The process of claim 1 wherein each of steps (a) and (b) are conducted at a pressure of from about 250 psi to about 400 psi.

19. The process of claim 1 wherein each of steps (a) and (b) are conducted in an enclosed vessel.

20. The process of claim 1 wherein said reaction product further comprises by-products, and wherein the process further comprises separating said 1,1-dichloro-3,3,3-trifluoropropane reaction product from said by-products.

21. The process of claim 1 wherein said reaction product comprises from about 40% to about 70% 1,1-dichloro-3,3,3-trifluoropropane.

22. The process of claim 1 wherein the reaction of step (b) is conducted in the liquid phase.

23. The process of claim 1 wherein steps (a) and (b) are conducted in a vessel that is tinder a vacuum.

24. A process for the preparation of 1,1-dichloro-3,3,3-trifluoropropane comprising:
   a) introducing a fluorination catalyst into a vessel;
   b) introducing hydrogen fluoride into the vessel under conditions sufficient to produce an activated fluorination catalyst;
   c) adding 1,1,1,3,3-pentachloropropane and hydrogen fluoride to said vessel under conditions sufficient for the 1,1,1,3,3-pentachloropropane and hydrogen fluoride to react in the presence of said activated fluorination catalyst, thereby forming a reaction product which comprises 1,1-dichloro-3,3,3-trifluoropropane; and thereafter
   d) recovering a composition consisting essentially of 1,1-dichloro-3,3,3-trifluoropropane from the reaction product.

25. The process of claim 24 wherein said reaction of step (c) is conducted in the liquid phase.

26. The process of claim 1 wherein 1,1-dichloro-3,3,3-trifluoropropane is obtained with a yield of at least about 40%.

27. The process of claim 1 wherein 1,1-dichloro-3,3,3-trifluoropropane is obtained with a yield of greater than 70%.

28. The process of claim 1 wherein pure 1,1-dichloro-3,3,3-trifluoropropane is recovered from the reaction product.

29. The process of claim 1 wherein 1,1-dichloro-3,3,3-trifluoropropane is obtained with a yield of at least about 40%.

30. The process of claim 1 wherein 1,1-dichloro-3,3,3-trifluoropropane is obtained with a yield of greater than 70%.

31. The process of claim 1 wherein pure 1,1-dichloro-3,3,3-trifluoropropane is recovered from the reaction product.

32. The process of claim 24 wherein pure 1,1-dichloro-3,3,3-trifluoropropane is recovered from the reaction product.

33. A process for the fluorination of 1,1,1,3,3-pentachloropropane to 1,1-dichloro-3,3,3-trifluoropropane comprising the steps of:
   (a) contacting a fluorination catalyst with hydrogen fluoride under conditions sufficient to produce an activated fluorination catalyst; and
   (b) reacting 1,1,1,3,3-pentachloropropane with hydrogen fluoride in the presence of said activated catalyst under conditions sufficient to produce a reaction product which comprises from about 40% to about 70% 1,1-dichloro-3,3,3-trifluoropropane; and then
   C) recovering 1,1-dichloro-3,3,3-trifluoropropane from the reaction product.

* * * * *